US012642924B2

(12) United States Patent
Gu

(10) Patent No.: US 12,642,924 B2
(45) Date of Patent: Jun. 2, 2026

(54) ATOMIZATION DEVICE AND COUNTER MODULE FOR THE SAME

(71) Applicant: SUZHOU SKYWELL HEALTHCARE INFORMATION CO., LTD., Suzhou (CN)

(72) Inventor: Yu Gu, Suzhou (CN)

(73) Assignee: SUZHOU SKYWELL HEALTHCARE INFORMATION CO., LTD., Suzhou (CN)

( * ) Notice: Subject to any disclaimer, the term of this patent is extended or adjusted under 35 U.S.C. 154(b) by 653 days.

(21) Appl. No.: 18/005,859

(22) PCT Filed: Jul. 8, 2021

(86) PCT No.: PCT/CN2021/105241
§ 371 (c)(1),
(2) Date: Jan. 18, 2023

(87) PCT Pub. No.: WO2022/017191
PCT Pub. Date: Jan. 27, 2022

(65) Prior Publication Data
US 2023/0285693 A1 Sep. 14, 2023

(30) Foreign Application Priority Data

Jul. 22, 2020 (CN) .......................... 202010710078.8

(51) Int. Cl.
*A61M 15/00* (2006.01)
*A61M 11/00* (2006.01)
(52) U.S. Cl.
CPC ...... *A61M 15/0071* (2014.02); *A61M 11/007* (2014.02); *A61M 15/0081* (2014.02); *A61M 2205/8281* (2013.01)

(58) Field of Classification Search
CPC .......... A61M 15/0071; A61M 15/0073; A61M 15/0076; A61M 15/0081
See application file for complete search history.

(56) References Cited

U.S. PATENT DOCUMENTS

2008/0210224 A1 9/2008 Brunnberg et al.
2008/0210228 A1 9/2008 Corbacho
(Continued)

FOREIGN PATENT DOCUMENTS

CN 203280860 U 11/2013
CN 103582505 A 2/2014
(Continued)

OTHER PUBLICATIONS

International Search Report of PCT/CN2021/105241, mailed on Sep. 28, 2021.
(Continued)

*Primary Examiner* — Kathryn E Ditmer
(74) *Attorney, Agent, or Firm* — Junhe Law Office P.C.; James J. Zhu

(57) ABSTRACT

The present application relates to an atomization device (100) and a counter module (114) for the same. The atomization device (100) comprises: an upper housing (102) and a lower housing (104), wherein the upper housing (102) is configured to mount a container (106) for containing liquid, and the container (106) is movable in an axial direction of the atomization device (100) between a release position and a stretch position, and wherein the stretch position is closer to a proximal end of the atomization device (100) than the release position; and the counter module (114) mounted inside the lower housing (104) and for counting the movement of the container (106) between the release position and the stretch position.

16 Claims, 7 Drawing Sheets

(56)          References Cited

U.S. PATENT DOCUMENTS

| | | | |
|---|---|---|---|
| 2010/0212664 A1* | 8/2010 | Bishop ................ | A61M 15/007 |
| | | | 128/200.23 |
| 2013/0074833 A1* | 3/2013 | Sieffert ............. | A61M 15/0076 |
| | | | 29/446 |
| 2014/0053838 A1* | 2/2014 | Berenshteyn ..... | A61M 15/0073 |
| | | | 128/203.15 |
| 2017/0072148 A1* | 3/2017 | Eicher ............... | A61M 15/0065 |
| 2017/0182268 A1* | 6/2017 | Mayer ................... | G06M 1/246 |
| 2020/0215275 A1* | 7/2020 | Kladders ........... | A61M 15/0065 |

FOREIGN PATENT DOCUMENTS

| | | | | | |
|---|---|---|---|---|---|
| CN | 106456908 A | | 2/2017 | | |
| CN | 109172960 A | | 1/2019 | | |
| CN | 109529160 A | * | 3/2019 | ........ | A61M 15/0071 |
| CN | 110944699 A | | 3/2020 | | |
| CN | 111032133 A | | 4/2020 | | |
| CN | 212383055 U | | 1/2021 | | |
| JP | 2007-527276 A | | 9/2007 | | |
| JP | 2017-514619 A | | 6/2017 | | |

OTHER PUBLICATIONS

The Office Action for the counterpart JP patent application 2023-504529, mailed on Apr. 1, 2025.

* cited by examiner

ATOMIZATION DEVICE AND COUNTER MODULE FOR THE SAME

FIELD OF THE INVENTION

The disclosure relates to the field of medical equipment, and more specifically, to an atomization device with a counter module.

BACKGROUND

Most commercially available medicinal aerosols do not have a dose counting function, and patients cannot predict the remaining amount of medicine when using the product. Therefore, it is easy to cause life-threatening or unnecessary trouble due to insufficient medicine during an acute attack. Many pharmaceutical companies are striving to integrate dose counting or indication mechanisms into their products to address the needs of patients. However, the existing aerosol products usually fix the dose counting mechanism and the container for containing the liquid medicine together, which reduces the versatility of the product.

Therefore, it is necessary to provide an improved counting mechanism for the atomization device.

SUMMARY

An objective of the present application is to provide an atomization device with a counter module.

In one aspect of the present application, an atomization device is provided. The atomization device comprises: an upper housing and a lower housing, wherein the upper housing is configured to mount a container for containing liquid, and the container is movable in an axial direction of the atomization device between a release position and a stretch position, and wherein the stretch position is closer to a proximal end of the atomization device than the release position; and a counter module mounted inside the lower housing and for counting the movement of the container between the release position and the stretch position, wherein the counter module comprises: a positioning shaft extending distally from an inner bottom surface of the lower housing; a rotatable sleeve sleeved outside the positioning shaft, wherein the rotatable sleeve is movable axially along the positioning shaft and rotatable about the positioning shaft, and wherein the rotatable sleeve has a movable serrated surface facing towards a distal end of the atomization device; a touching member coupled to a distal end of the positioning shaft, wherein the touching member is movable axially along the positioning shaft and not rotatable about the positioning shaft, and the touching member comprises a flange operably engagable with the movable serrated surface; and wherein in response to that the container is moved to a position close to the stretch position so that the flange is at least partially engaged with the movable serrated surface, the flange and the movable serrated surface which are mutually engaged generate a circumferential force that rotates the rotatable sleeve; a slidable ring sleeved outside the rotatable sleeve and threadedly coupled to the rotatable sleeve, and wherein the slidable ring is movable axially along the positioning shaft but is not rotatable about the positioning shaft; and a bias spring mounted outside the positioning shaft, with a first end abutting against the inner bottom surface of the lower housing and a second end abutting against the rotatable sleeve; wherein the rotatable sleeve is pressed by the touching member and moves proximally to compress the bias spring in response to that the container moves from the release position to the stretch position; the rotatable sleeve is no longer pressed by the touching member so that the bias spring is released to push the rotatable sleeve to move distally in response to that the container moves from the stretch position to the release position; during at least a part of the axial movement of the rotatable sleeve, the circumferential force generated by the flange and the movable serrated surface which are mutually engaged drives the rotatable sleeve to rotate relative to the slidable ring and changes an axial position of the slidable ring on the rotatable sleeve.

In some embodiments, the counter module further comprises a locking mechanism configured to limit a moving distance of the slidable ring along the rotatable sleeve.

In some embodiments, the slidable ring is threadedly coupled to the rotatable sleeve such that the slidable ring moves proximally, and the locking mechanism is disposed on the inner bottom surface of the lower housing.

In some embodiments, the slidable ring is threadedly coupled to the rotatable sleeve such that the slidable ring moves distally, and the locking mechanism is disposed on an upper housing or a bottom surface of the container.

In some embodiments, the counter module further comprises: a positioning rib disposed inside the lower housing and extending in the axial direction of the atomization device, wherein the positioning rib is configured to couple with the slidable ring at a predetermined circumferential position of the slidable ring, and to limit the rotation of the slidable ring about the positioning shaft.

In some embodiments, the counter module further comprises: a positioning ring mounted outside the positioning shaft and having an annular protrusion facing the inner bottom surface of the lower housing, wherein the positioning ring is configured to prevent the axial movement of the rotatable sleeve from disengaging from the positioning shaft.

In some embodiments, the annular protrusion has a fixed serrated surface that matches the movable serrated surface of the rotatable sleeve, the fixed serrated surface and the movable serrated surface are in contact with each other to limit the rotation of the rotatable sleeve about the positioning shaft in response to that the container moves to a position close to the release position so that the flange no longer engages with the movable serrated surface.

In some embodiments, the flange has a wavy lower surface engagable with the movable serrated surface of the rotatable sleeve, and the wavy lower surface engages with the movable serrated surface to generate the circumferential force.

In some embodiments, the touching member further comprises a piercing element disposed on a distal end surface of the touching member, and the piercing element is configured to open or pierce the container in response to that the touching member contacts with the container.

In some embodiments, a movement stroke of the touching member along the positioning shaft is greater than that of the rotatable sleeve along the positioning shaft.

In some embodiments, the container and the counter module are separated from each other.

In some embodiments, the container and the counter module are pre-assembled as an integral member.

In some embodiments, the lower housing comprises an observation window on its side wall, through which a position of the rotatable sleeve on the positioning shaft can be observed.

In some embodiments, the lower housing is transparent.

In some embodiments, the lower housing is rotatable relative to the upper housing to drive the container to move in the axial direction of the atomization device.

In another aspect of the present application, a counter module for an atomization device is provided. The atomization device has a container which is movable in an axial direction of the atomization device between a release position and an stretch position, wherein the stretch position is closer to the proximal direction than the release position; and the counter module is mounted inside the atomization device for counting the movement of the container between the release position and the stretch position, wherein the counter module includes: a positioning shaft extending from the inner bottom surface of the atomization device in a distal direction; a rotatable sleeve which is sleeved on the positioning shaft and which is movable axially along the positioning shaft and rotate about the positioning shaft, wherein the rotatable sleeve has a movable serrated surface facing the distal direction; a touching member which is coupled to the distal end of the positioning shaft and which is movable axially along the positioning shaft but is not rotatable about the positioning shaft, and the touching member which includes a flange capable of operably engagable with the movable serrated surface; in response to that the container is moved to a position close to the stretch position so that the flange is at least partially engaged with the movable serrated surface, the flange and the movable serrated surface which are mutually engaged generate a circumferential force that makes the rotatable sleeve rotate; a slidable ring which is sleeved on the rotatable sleeve and which is threadedly coupled to rotatable sleeve, and the slidable ring which is movable axially along the positioning shaft but is not rotatable about the positioning shaft; and a bias spring which is mounted on the positioning shaft, one end of the bias spring can abut against the inner bottom surface of the atomization device, and the other end of the bias spring can abut against the rotatable sleeve; wherein the rotatable sleeve is pressed by the touching member and moves proximally to compress the bias spring in response to that the container moves from the release position to the stretch position; the rotatable sleeve is no longer pressed by the touching member so that the bias spring is released to push the rotatable sleeve to move in the distal direction in response to that the container moves from the stretch position to the release position; during at least a part of the axial movement of the rotatable sleeve, the circumferential force generated by the flange and the movable serrated surface which are mutually engaged drives the rotatable sleeve to rotate relative to the slidable ring and makes the axial position of the slidable ring on the rotatable sleeve change.

The above is an overview of the present application, and may be simplified, summarized and omitted in detail. Therefore, those skilled in the art should recognize that this section is only illustrative, and is not intended to limit the scope of the present application in any way. This summary section is neither intended to determine the key features or essential features of the subject matter sought for protection, nor is it intended to be used as an auxiliary means to determine the scope of the subject matter sought for protection.

BRIEF DESCRIPTION OF THE DRAWINGS

The above and other features of the content of the present application will be more fully understood through the following description and appended claims in combination with the drawings. It can be understood that these drawings only illustrate several implementations of the content of the present application, and therefore should not be considered as limiting the scope of the content of the present application. By adopting the drawings, the content of the present application will be explained more clearly and in detail.

DETAILED DESCRIPTION OF THE DRAWINGS

Figure 1:
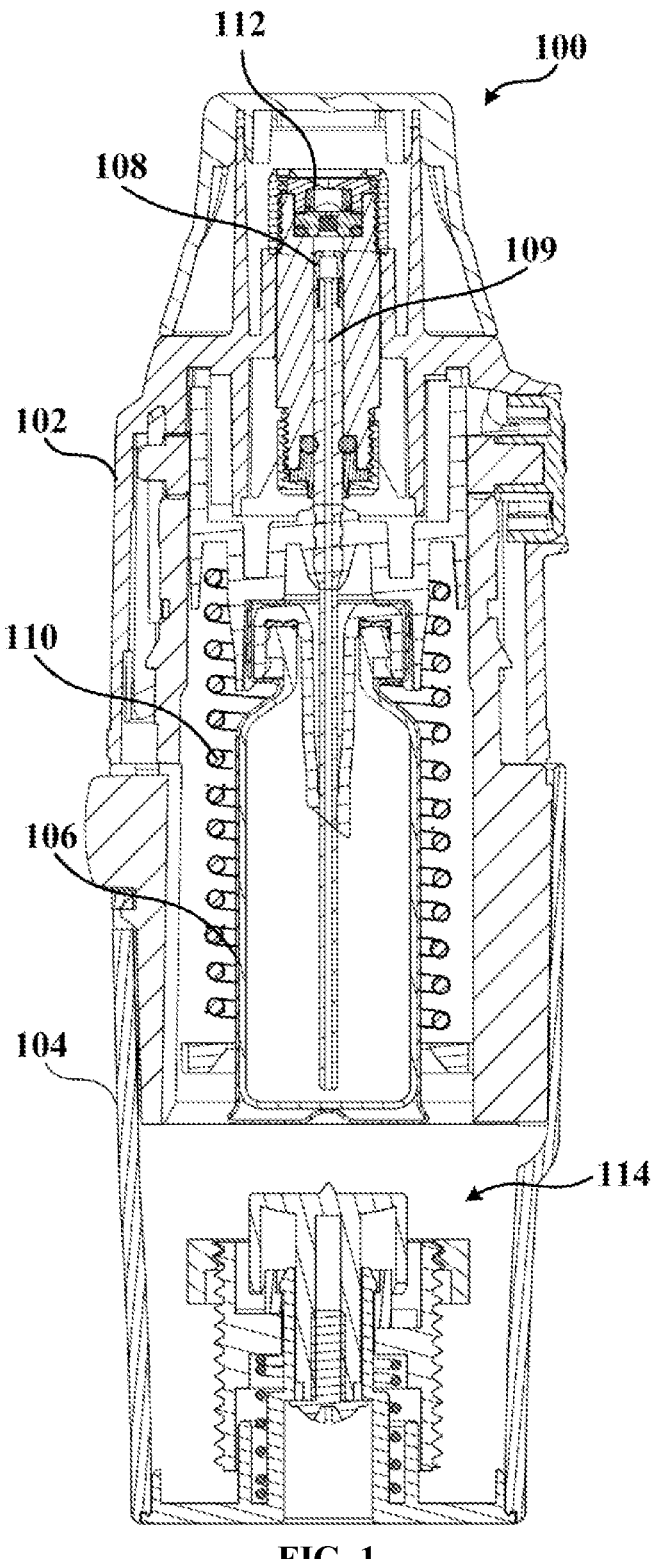
FIG. 1 shows an atomization device 100 according to an embodiment of the present application, which is not in use, and the container thereon is in a release position.

The following detailed description refers to the drawings constituting a part thereof. In the drawings, similar symbols usually indicate similar components, unless the context specifies otherwise. The illustrative embodiments described in the detailed description, drawings, and claims are not intended to limit. Without departing from the spirit or scope of the subject matter of the present application, other embodiments may be adopted, and other changes may be made. It can be understood that various aspects of the content of the present application generally described in the present application and illustrated in the drawings can be configured, replaced, combined, and designed with various different configurations, and all of these clearly constitute a part of the content of the present application.

FIG. 1 shows an atomization device 100 according to an embodiment of the present application, wherein the atomization device 100 is not in use. The atomization device 100 is designed to be capable of multiple administrations, and each administration operation will deliver a part of the liquid medicine contained therein in a spray manner, for example, to be provided to a patient.

As shown in FIG. 1, the atomization device 100 comprises an upper housing 102 and a lower housing 104 that can rotate relatively. A container 106 is mounted on the upper housing 102, which is configured to contain liquid, such as a liquid medicine. In some embodiments, the container 106 is removably coupled to the upper housing 102, so that after the liquid medicine in the container 106 is used up, the container 106 is removable from the upper housing 102 and replaced with a new liquid storage container. Optionally, the container 106 may be threadedly or snappily coupled to the upper housing 102. The upper housing 102 is also provided with a liquid channel 108, which is provided with a hollow plunger 109 that is movable in an axial direction of the atomizing device 100 relative to the liquid channel 108, and provided at its distal end with a one-way valve that allows the liquid to flow in one direction. The one-way valve only allows liquid to flow from the inner channel of the hollow plunger 109 to the distal end of the liquid channel 108 through it, but does not allow the liquid to flow in the reverse direction. Therefore, when the container 106 and the hollow plunger 109 are movable axially relative to the liquid channel 108, the liquid will be pumped from the container 106 into the liquid channel 108, and then be squeezed from the liquid channel 108 distally.

Figure 4:
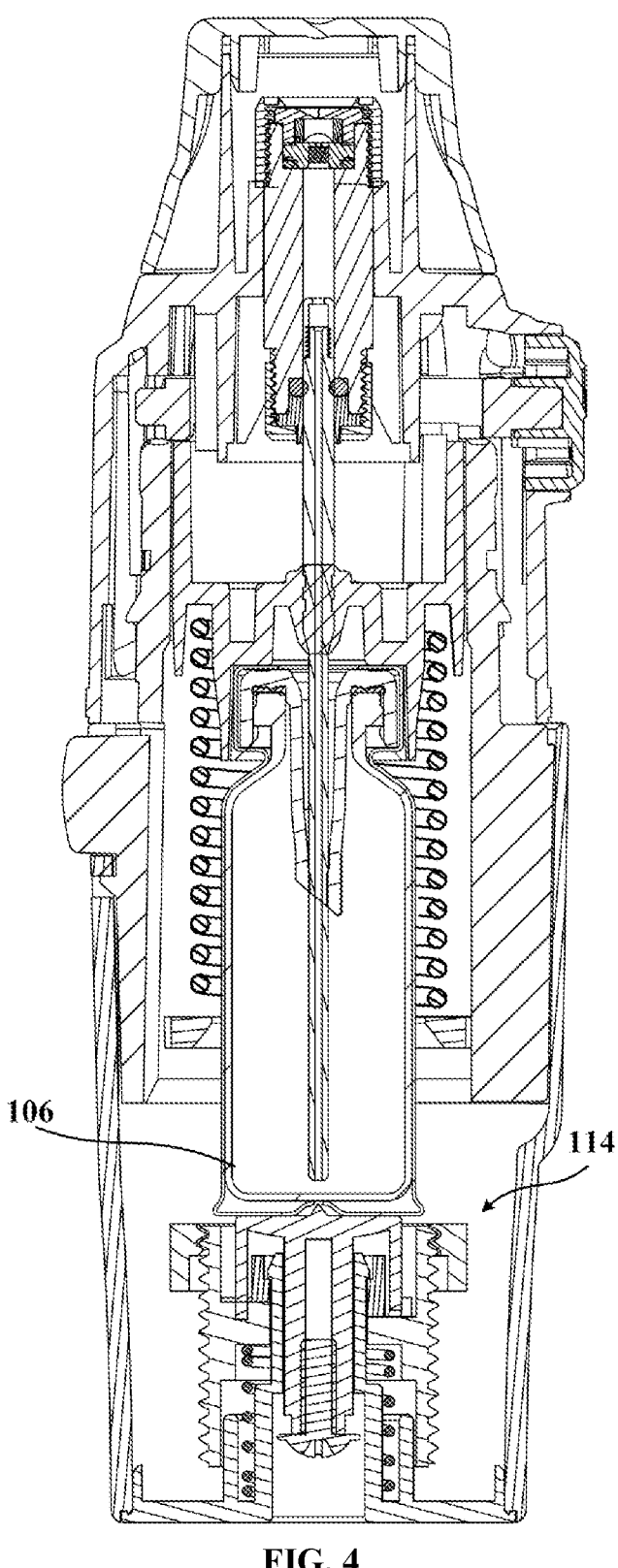
FIG. 4 shows the atomization device 100 shown in FIG. 1 with the container thereon in a stretch position.

In some embodiments, the upper housing 102 and the lower housing 104 is rotatable relatively, so that the container 106 and the hollow plunger 109 are movable axially relative to the lower housing 104, for example, moving toward the lower housing 104, moving from the release position shown in FIG. 1 toward a stretch position closer to the proximal end (see FIG. 4). Wherein, the relative rotation of the upper housing 102 and the lower housing 104 can be a part or all of at least one of the two relative to a part or all of the rotation of the other, as long as the axial position of the container 106 in the atomization device 100 changes.

In addition, the atomization device 100 further comprises an atomization spring 110 disposed on the upper housing 102. During the aforementioned the container 106 moving proximally, the atomization spring 110 can be compressed to accumulate energy, and the liquid in the container 106 is pumped into the liquid channel 108 at the same time. After the container 106 moves to the stretch position, the user can operate to release the compressed atomization spring 110, so that the atomization spring 110 can push the container 106 from the stretch position to the release position and push the liquid contained in the liquid channel 108 to be ejected through the atomization nozzle 112. It can be understood that one reciprocating movement of the container 106 between the release position and the stretch position completes a drug delivery operation. In some other embodiments, the upper housing 102 and the lower housing 104 are also movable relative to each other in other ways, such as relative axial movement, so as to drive the container 106 to move reciprocatedly between the release position and the stretch position.

It is expected that the counter module 114 of the atomization device 100 can be configured to count the administration operations of the atomization device 100. When the container 106 moves close to the stretch position each time, the counter module 114 may be activated and change the state.

Figure 2:
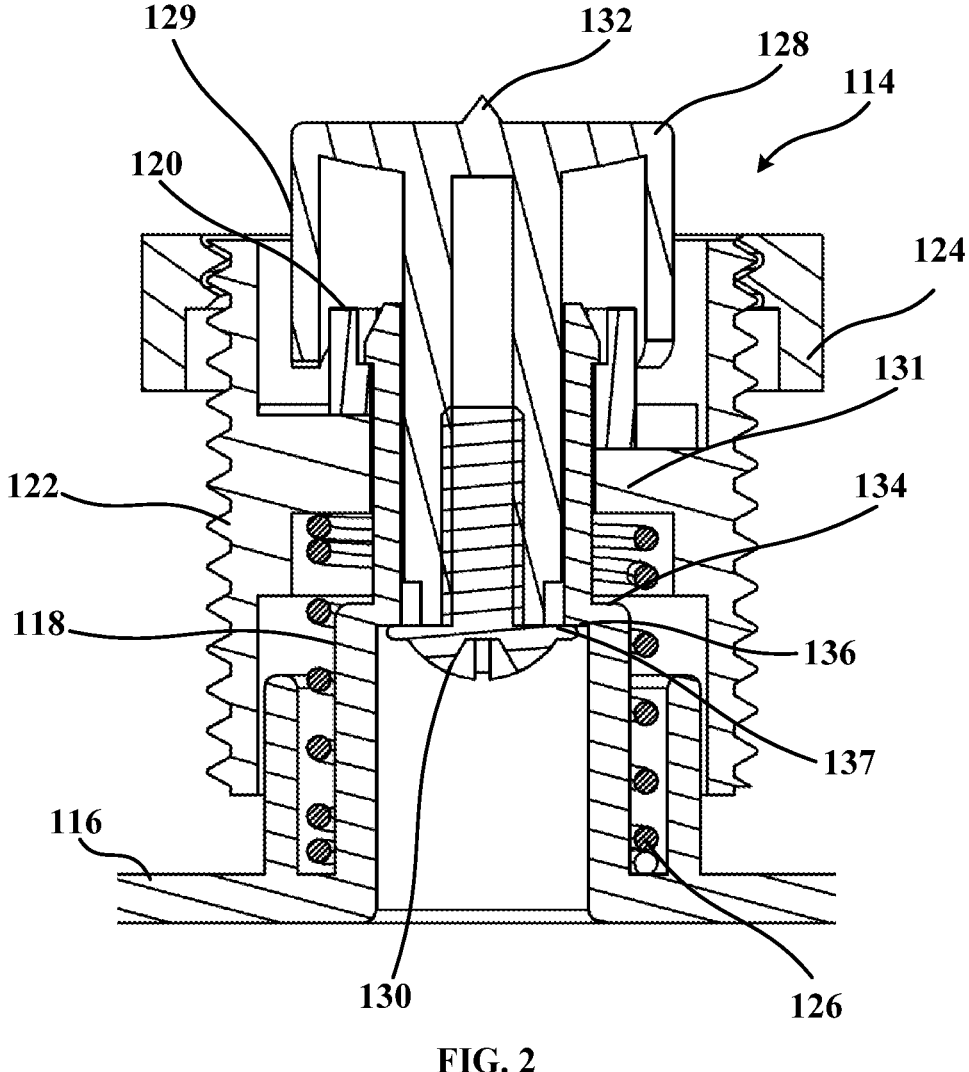
FIG. 2 shows an enlarged view of the counter module of the atomization device shown in FIG. 1.
Figure 3:
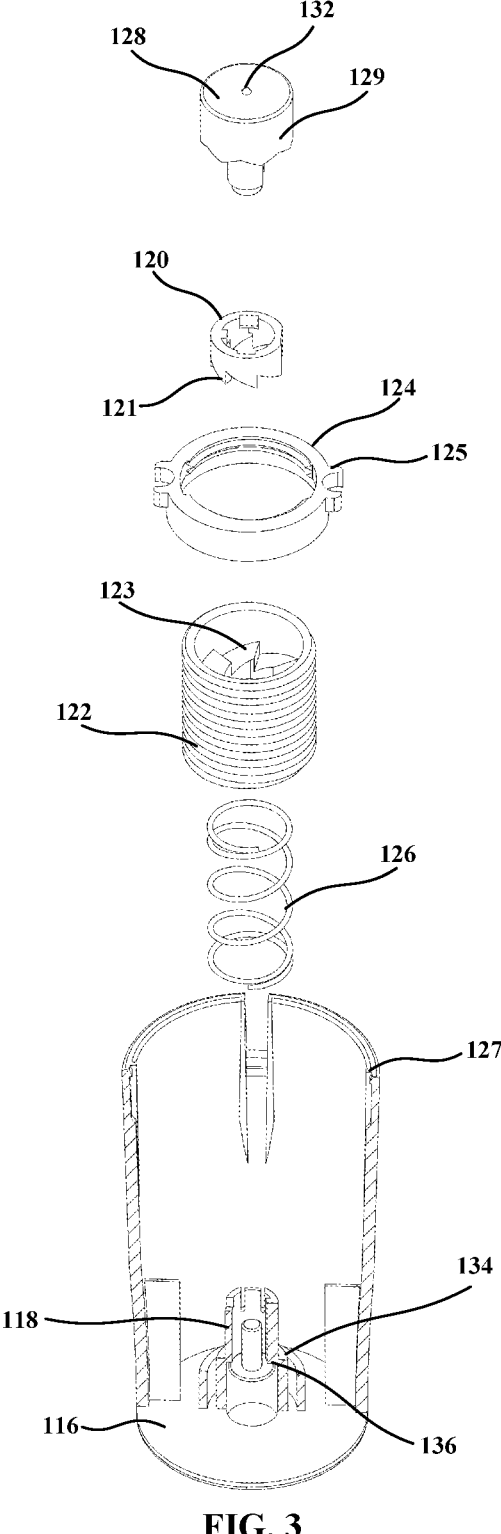
FIG. 3 shows an exploded view of the atomization device shown in FIG. 1.

FIG. 2 shows a schematic cross-sectional view of the counter module 114 shown in FIG. 1, while FIG. 3 shows an exploded view of the counter module 114.

As shown in FIGS. 2 and 3, the counter module 114 is disposed on the inner bottom surface 116 of the lower housing. The counter module 114 comprises a positioning shaft 118 extending from the inner bottom surface 116 of the lower housing distally. A positioning ring 120 is mounted on the positioning shaft 118, which can be mounted at the distal end of the positioning shaft 118 by, for example, a snap coupling. In some embodiments, the positioning ring 120 is fixedly mounted on the positioning shaft 118. The positioning ring 120 has a protrusion 121 facing the inner bottom surface 116 of the lower housing, which may be configured in a ring shape, for example. In some embodiments, the annular protrusion 121 has a fixed serrated surface facing the inner bottom surface 116 of the lower housing.

A rotatable sleeve 122 and a bias spring 126 are also sleeved on the positioning shaft 118. In the embodiments shown, the rotatable sleeve 122 and the bias spring 126 are both sleeved on the outside of the positioning shaft 118, but those skilled in the art can sleeve these components in other sleeve ways, for example, the rotatable sleeve 122 and the bias spring 126 are sleeved on the inner side of the positioning shaft 118, and accordingly, the positions of other components can also be adjusted. The rotatable sleeve 122 is disposed between the inner bottom surface 116 and the positioning ring 120, and can be operatively coupled with the positioning ring 120, and is restricted from being separated from the positioning shaft 118 by the annular protrusion 121. In some embodiments, the rotatable sleeve 122 may have a sleeve having a diameter larger than the outer diameter of the positioning shaft 118, and the inner side of the sleeve may have an inner support portion extending toward the positioning shaft 118, wherein the inner diameter of the inner support portion is substantially the same as the outer diameter of the corresponding portion of the positioning shaft 118 so as to limit the linear movement of the positioning shaft 118 in the non-axial direction. The bias spring 126 is disposed between the inner bottom surface 116 and the rotatable sleeve 122. One end of the bias spring 126 can abut against the inner bottom surface 116 of the lower housing, and the other end can abut against the rotatable sleeve 122. Therefore, the axial movement of the rotatable sleeve 122 may be related to the state of the bias spring 126. Specifically, the rotatable sleeve 122 is movable in an axial direction of the atomization device between the inner bottom surface 116 and the positioning ring 120: when the rotatable sleeve 122 is compressed and moved proximally, the bias spring 126 is compressed; and when the rotatable sleeve 122 is no longer subjected to the compressing force proximally, the bias spring 126 can be released, thereby driving the rotatable sleeve 122 to move distally.

Still referring to FIGS. 2 and 3, the counter module 114 further comprises a touching member 128 for operatively compressing the rotatable sleeve 122 when the container moves toward the lower housing. Specifically, the touching member 128 is coupled to the distal end of the positioning shaft 118 and is movable in an axial direction of the atomization device for a certain distance. In some embodiments, the touching member 128 may be coupled with the locking screw 130 so as to be operably mounted at the distal end of the positioning shaft 118. In the embodiments shown in FIGS. 2 and 3, the touching member 128 is generally configured as a sleeve structure having a flange 129, wherein the flange 129 is disposed outside the distal end of the touching member 128, and the sleeve structure can be inserted into the positioning shaft 118 and coupled with the locking screw 130 on the opposite side. As such, the flange 129 can limit the touching member 128 from moving proximally to the length of the positioning shaft 118, and the locking screw 130 can limit the touching member 128 from moving distally to the length of the positioning shaft 118. Wherein, the circumferential movement of the touching member 128 is locked, for example, the touching member 128 and the positioning shaft 118 are provided with a matching structure of protruding teeth and axially extending grooves, so that the touching member 128 is not rotatable about the positioning shaft 118.

Figure 5:
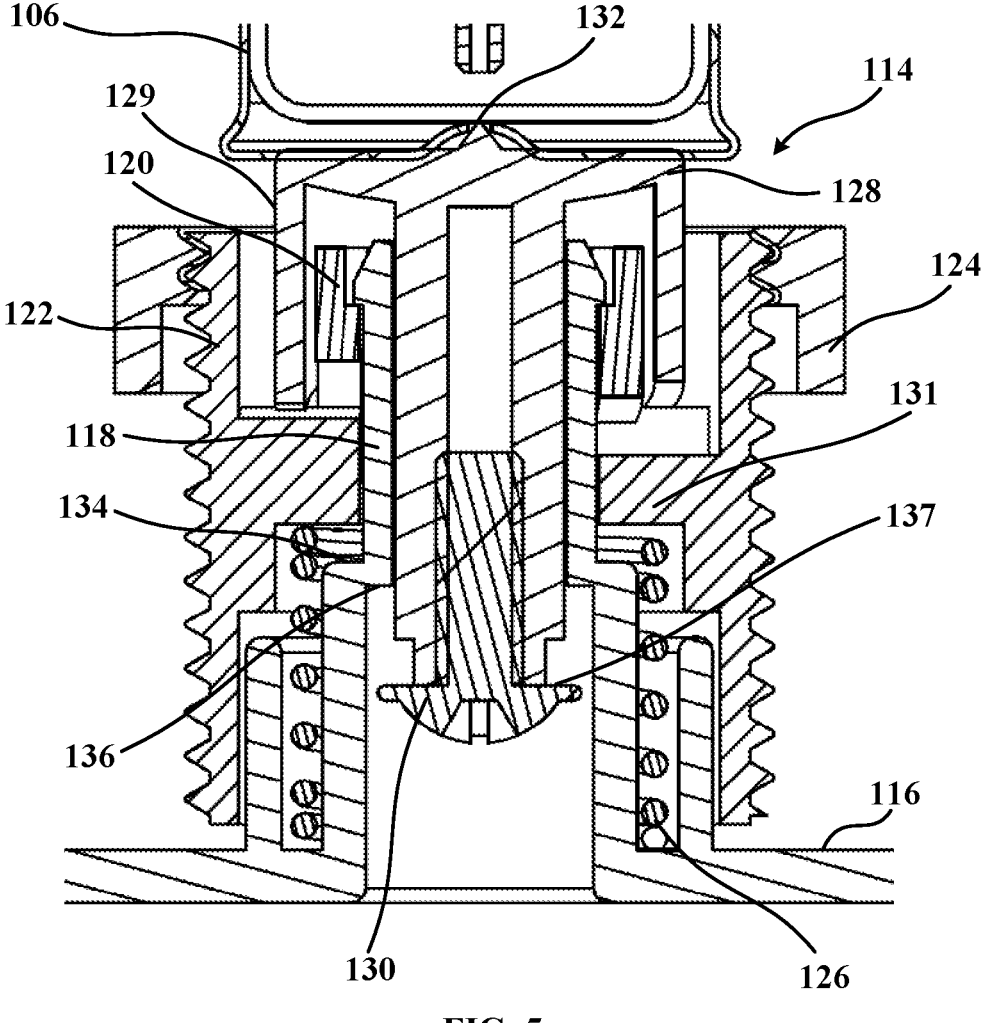
FIG. 5 shows an enlarged view of the counter module of the atomization device shown in FIG. 4.

The touching member 128 can compress the rotatable sleeve 122 to move it proximally to a position close to the inner bottom surface 116 of the lower housing, which generally corresponds to the container in a stretch position. FIG. 4 shows a schematic diagram of the container on the atomization device 100 shown in FIG. 1 in a stretch position, and FIG. 5 shows an enlarged view of the counter module of the atomization device shown in FIG. 4. As shown in FIGS. 4 and 5, when the container 106 is in the stretch position, it can contact with and compress the touching member 128, which causes the touching member 128 to move proximally and thorough the positioning shaft 118, thereby contacting with and compressing the lower surface of the flange 129 on the touching member 128 compresses the rotatable sleeve 122. As such, the rotatable sleeve 122 and the slidable ring 124 threadedly coupled thereto move proximally together, and at the same time compress the bias spring 126. In some embodiments, the proximal end of the positioning shaft 118 has a diameter slightly larger than the distal end, so that it forms an outer limiting surface 134 on the outer surface of the positioning shaft 118 and an inner limiting surface 136 on the inner surface of the positioning shaft 118. The outer limiting surface 134 can abut against the lower bottom surface of the inner support portion 131 of the rotatable sleeve 122 to prevent the rotatable sleeve from moving proximally.

In another aspect, as shown in FIG. 2, when the touching member 128 moves distally, the bottom surface 137 of the screw head of the locking screw 130 can abut against the inner limiting surface 136 to prevent the touching member 128 from being separated from the positioning shaft 118. In some embodiments, the distance between the lower bottom surface of the inner support portion 131 of the rotatable sleeve 122 and the outer limiting surface 134 is smaller than the distance between the inner limiting surface 136 and the bottom surface 137 of the screw head. As such, a movement stroke of the touching member 128 on the positioning shaft 118 is greater than the movement stroke of the rotatable sleeve 122 on the positioning shaft 118.

As shown in FIGS. 2, 3 and 4, the flange 129 of the touching member 128 may have a wavy lower surface. When the touching member 128 contacts with the rotatable sleeve 122, the wavy lower surface is engagable with the movable serrated surface 123. When the container 106 contacts with the touching member 128 and compresses the rotatable sleeve 122 proximally, the engagable wavy lower surface and the movable serrated surface 123 will cause the touching member 128 and the rotatable sleeve 122 to move toward each other to decompose and generate a circumferential force. However, since the circumferential movement of the touching member 128 is locked, only the rotatable sleeve 122 is rotatable about the positioning shaft 118. Similarly, when the container 106 leaves the touching member 128, the rotatable sleeve 122 is no longer compressed by the touching member 128, but is pushed by the bias spring 126 to move distally; during this process, especially when the touching member 128 is still at a position close to the distal end, the flange 129 which engages with each other and the movable serrated surface 123 decompose the supporting force and generate a circumferential force, so that the rotatable sleeve 122 rotates about the positioning shaft 118.

A slidable ring 124 is sleeved outside the rotatable sleeve 122, which is threadedly coupled with the rotatable sleeve 122, so that it is rotatable relative to the rotatable sleeve 122 and move axially. The slidable ring 124 has one or more positioning blocks 125 corresponding to one or more predetermined circumferential positions thereof. In the embodiment shown in FIG. 3, the slidable ring 124 has two positioning blocks 125 provided substantially at an interval of 180 degrees. The positioning block 125 can be coupled with the positioning rib 127 at the corresponding position extending in an axial direction of the atomization device inside the lower housing, thereby limiting the slidable ring 124 to only be movable axially along the positioning shaft 118 and is not rotatable about the positioning shaft 118. In the embodiment shown in FIG. 3, the positioning block 125 is configured as a recess, and the positioning rib 127 is configured as a convex strip that can be embedded in the recess. In some other embodiments, the positioning block 125 may also be configured as a protrusion, and the positioning rib 127 may be configured as an axially extending groove structure. Those skilled in the art can understand that various alternative implementations can be used for the matching structure of the positioning rib and the positioning block.

When the rotatable sleeve 122 is disposed close to the proximal end, it will be rotated by the circumferential force. At this time, the slidable ring 124 is limited by the positioning ribs 127 and is not rotatable about the positioning shaft 118, thereby the rotatable sleeve 122 and the slidable ring 124 rotate relative to each other. Since the rotatable sleeve 122 and the slidable ring 124 are threadedly coupled to each other, the relative rotation of the slidable ring 124 will cause the axial position of the slidable ring 124 on the rotatable sleeve 122 to change, that is, the slidable ring 124 is screwed to a certain distance on the rotatable sleeve 122. It can be understood that the distance of the slidable ring 124 screwed on the rotatable sleeve 122 depends on parameters such as the pitch of the thread, the lead angle, and the axial movement distance of the rotatable sleeve 122, and those skilled in the art can adjust these parameters according to actual needs. It can be understood that each atomization operation of the atomization device can cause the slidable ring 124 to screw a certain distance on the rotatable sleeve 122, and the rotatable sleeve 122 has a predetermined axial length, so that the distance of slidable ring 124 screwed can be configured to characterize the number of atomization operations. In other words, the longer the distance of the slidable ring 124 screwed, the greater the number of atomization operations. In some embodiments, the lower housing may include an observation window on its side wall, through which the position of the rotatable sleeve on the positioning shaft can be observed. The observation window can be transparent or notched. In other embodiments, the lower housing may be transparent.

It can be understood that when the container 106 moves to a position close to the release position so that the flange 129 no longer engages with the movable serrated surface 123, the fixed serrated surface and the movable serrated surface 123 on the positioning ring 120 are aligned with and contact with each other to limit the rotation of the rotatable sleeve 122 about the positioning shaft 118. The fixed serration surface and the movable serration surface 123 may have a matching shape and/or tooth pitch.

As shown in FIGS. 2, 3 and 5, the distal end surface of the touching member 128 has a piercing element 132. When the touching member 128 contacts with the container 106 as shown in FIG. 5, the piercing element 132 can open or pierce the container 106. Generally, when not in use, the container 106 is provided with a sealing film or similar sealing member. After the piercing element 132 pierces the sealing member, the container 106 can be opened, so that the liquid contained in the container 106 can be pumped out of the container 106 through a subsequent pumping operation. It can be understood that the container 106 is in the released position shown in FIG. 1 before being in use. At this time, due to the limit between the bottom surface of the screw head and the inner limiting surface, the container 106 will not contact with the touching member 128, and therefore it will not be pierced and opened by the piercing element 132 either.

FIGS. 1 and 4 show part of the state of the counter module during an atomization operation. As mentioned above, after each atomization operation, the slidable ring on the counter module will move a certain distance proximally. In some embodiments, the counter module may further comprise a locking mechanism configured to limit the moving distance of the slidable ring on the rotatable sleeve. In other words, the number of atomization operations can be determined by the moving distance of the slidable ring, and the limiting mechanism can limit the atomization device to no longer be able to continue the atomization operation when the atomization device exceeds a certain number of uses.

Figure 6:
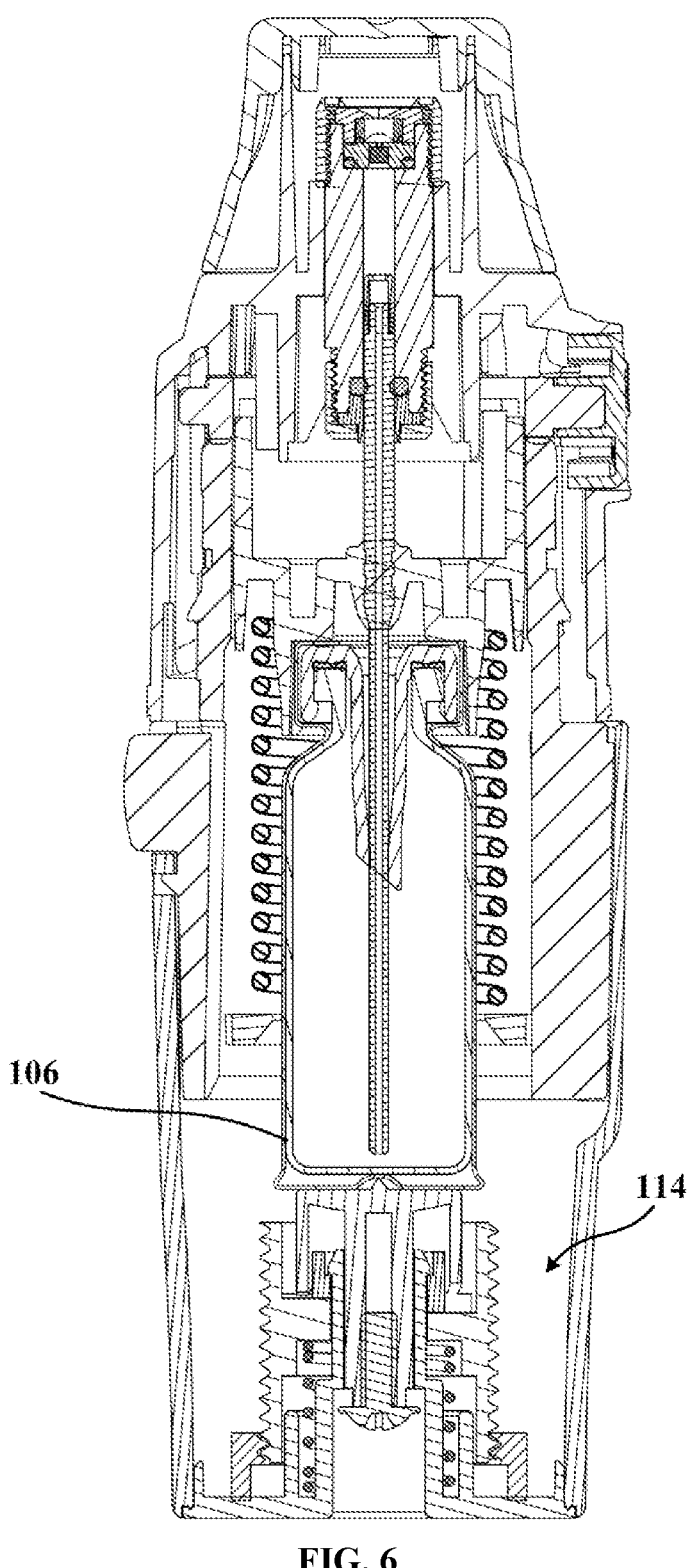
FIG. 6 shows the atomization device 100 shown in FIG. 1, with the container thereon close to the stretch position shown in FIG. 4, but the counter module is locked.
Figure 7:
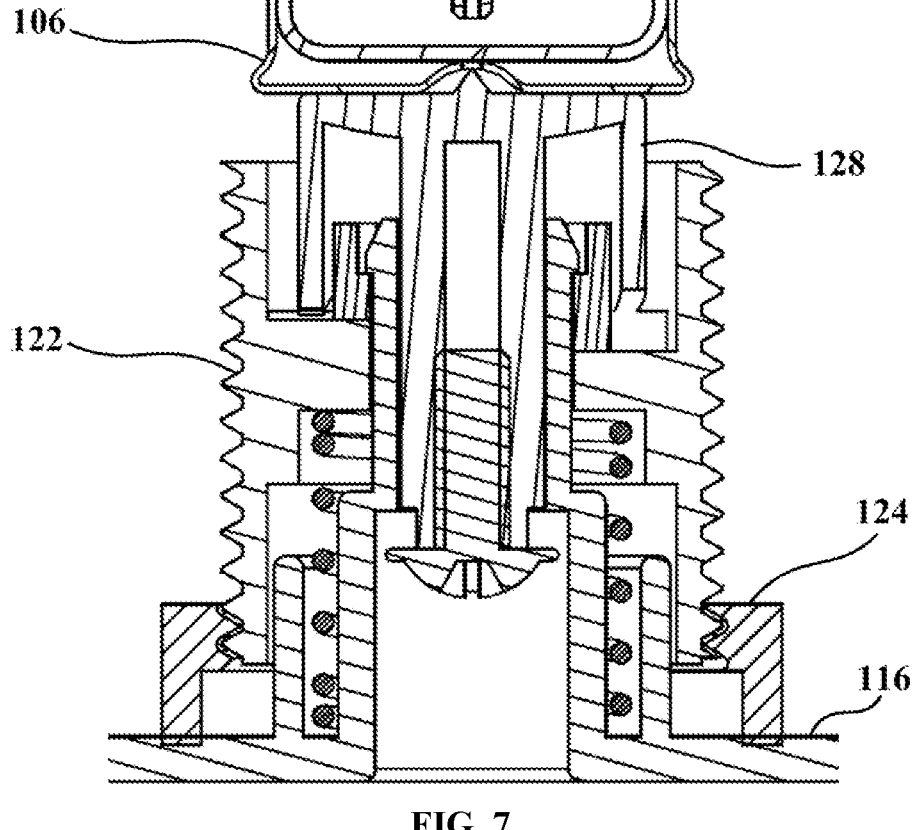
FIG. 7 shows an enlarged view of the counter module of the atomization device shown in FIG. 6.

FIG. 6 shows a schematic diagram of the counter module of the atomization device being locked, when the container is generally close to the stretch position. It can be seen that when the container reaches the stretch position shown in FIG. 4, it will end at the upper surface of the touching member, so that the upper and lower housings of the atomization device cannot continue to rotate relative to each other, and the atomization spring cannot be fully compressed, and the release button cannot pop up, which makes the atomization device unable to work normally. Wherein, the release button is an operation mechanism configured to control the release of the atomization spring. FIG. 7 is an enlarged schematic diagram of FIG. 6, which more clearly shows a schematic diagram of the container and the touching member partially interfering with each other.

For the counter module in the atomization device shown in FIGS. 6 and 7, compared to the schematic diagram of the initial operation shown in FIGS. 1 and 2, the slidable ring 124 moves axially toward the proximal end along the rotatable sleeve 122, so that the lower bottom surface and the inner bottom surface 116 of the lower housing abut against each other. In this case, the locking mechanism is disposed on the inner bottom surface of the lower housing. At this time, when the container 106 is subjected to a force toward the proximal end, it will abut against the touching member 128. However, since the slidable ring 124 abuts against the inner bottom surface 116 of the lower housing at the same time, neither the touching member 128 nor the container 106 is movable proximally, so that the container 106 is locked to limit its movement to the stretch position.

It can be understood by those skilled in the art that, in some alternative embodiments, the threaded coupling of the slidable ring and the rotatable sleeve can be configured that the slidable ring is movable distally to a predetermined position. At this time, the locking mechanism can be disposed on the bottom surface of the upper housing or the container.

In the foregoing embodiments, the container and the counter module are designed to be separated, so that the counter module is reusable. It can be understood that in some other embodiments, the container and the counter module may be pre-assembled as an integral component, so that each counter module and the container are for one-time use.

The above is an overview of the present application, which may be simplified, summarized and omitted in detail. Therefore, those skilled in the art should realize that this portion is only illustrative, and is not intended to limit the scope of the present application in any way. This summary is neither intended to determine the key features or essential features of the subject matter sought for protection, nor is it intended to be used as an auxiliary means to determine the scope of the subject matter sought for protection.

It should be noted that although several components or subcomponents of the atomization device are mentioned in the above detailed description, this division is only exemplary and not mandatory. In fact, according to the embodiments of the present application, the features and functions of two or more components described above may be embodied in one component. In contrast, the features and functions of one component described above can be further divided into multiple components to be embodied.

Those skilled in the art can understand and implement other changes to the disclosed embodiments by studying the specification, the disclosure, the drawings and the appended claims. In the claims, the phrase "comprise" or "include" does not exclude other elements and steps, and the phrase "a" and "an" do not exclude plurals. In the actual application of the present application, one part may perform the functions of multiple technical features referred in the claims. Any reference numerals in the claims should not be considered as limiting the scope.

What is claimed is:

1. An atomization device, wherein the atomization device comprises:

an upper housing and a lower housing, wherein the upper housing is configured to mount a container for containing liquid, and the container is movable in an axial direction of the atomization device between a release position and a stretch position, and wherein the stretch position is closer to a proximal end of the atomization device than the release position; and a counter module mounted inside the lower housing and for counting the movement of the container between the release position and the stretch position, wherein the counter module comprises:

a positioning shaft extending distally from an inner bottom surface of the lower housing;

a rotatable sleeve sleeved outside the positioning shaft, wherein the rotatable sleeve is movable axially along the positioning shaft and rotatable about the positioning shaft, and wherein the rotatable sleeve has a movable serrated surface facing towards a distal end of the atomization device;

a touching member coupled to a distal end of the positioning shaft, wherein the touching member is movable axially along the positioning shaft and not rotatable about the positioning shaft, and the touching member comprises a flange operably engagable with the movable serrated surface; and wherein, in response to that the container is moved towards the stretch position so that the flange is at least partially engaged with the movable serrated surface, the flange and the movable serrated surface, when mutually engaged, are configured to generate a circumferential force that rotates the rotatable sleeve;

a slidable ring sleeved outside the rotatable sleeve and threadedly coupled to the rotatable sleeve, and wherein the slidable ring is movable axially along the positioning shaft but is not rotatable about the positioning shaft; and a bias spring mounted outside the positioning shaft, with a first end abutting against the inner bottom surface of the lower housing and a second end abutting against the rotatable sleeve; wherein the rotatable sleeve is configured to be pressed by the touching member and move proximally to compress the bias spring in response to that the container moves from the release position to the stretch position; the rotatable sleeve is configured to be no longer pressed by the touching member so that the bias spring is released to push the rotatable sleeve to move axially towards the distal end of the atomization device in response to that the container moves from the stretch position to the release position; during at least a part of the axial movement of the rotatable sleeve, the circumferential force configured to be generated by the flange and the movable serrated surface, when mutually engaged, is configured to drive the rotatable sleeve to rotate relative to the slidable ring and change an axial position of the slidable ring on the rotatable sleeve.

2. The atomization device of claim 1, wherein the counter module further comprises a locking mechanism configured to limit a moving distance of the slidable ring along the rotatable sleeve.

3. The atomization device of claim 2, wherein the slidable ring is threadedly coupled to the rotatable sleeve such that the slidable ring is configured to move proximally, and the locking mechanism incorporates the inner bottom surface of the lower housing.

4. The atomization device of claim 2, wherein the slidable ring is threadedly coupled to the rotatable sleeve such that the slidable ring is configured to move distally, and the locking mechanism incorporates an upper housing or a bottom surface of the container.

5. The atomization device of claim 1, wherein the counter module further comprises:

a positioning rib disposed inside the lower housing and extending in the axial direction of the atomization device, wherein the positioning rib is configured to couple with the slidable ring at a predetermined circumferential position of the slidable ring, and to limit the rotation of the slidable ring about the positioning shaft.

6. The atomization device of claim 1, wherein the counter module further comprises:

a positioning ring mounted outside the positioning shaft and having an annular protrusion facing the inner bottom surface of the lower housing, wherein the positioning ring is configured to prevent the axial movement of the rotatable sleeve from disengaging from the positioning shaft.

7. The atomization device of claim 6, wherein the annular protrusion has a fixed serrated surface that matches the movable serrated surface of the rotatable sleeve, the fixed serrated surface and the movable serrated surface are configured to be in contact with each other to limit the rotation of the rotatable sleeve about the positioning shaft in response to that the container moves towards the release position so that the flange no longer engages with the movable serrated surface.

8. The atomization device of claim 1, wherein the flange has a wavy lower surface engagable with the movable serrated surface of the rotatable sleeve, and the wavy lower surface is configured to engage with the movable serrated surface to generate the circumferential force.

9. The atomization device of claim 1, wherein the touching member further comprises a piercing element disposed on a distal end surface of the touching member, and the piercing element is configured to open or pierce the container in response to that the touching member contacts with the container.

10. The atomization device of claim 1, wherein a movement stroke of the touching member along the positioning shaft is configured to be greater than that of the rotatable sleeve along the positioning shaft.

11. The atomization device of claim 1, wherein the container and the counter module are separable from each other.

12. The atomization device of claim 1, wherein the container and the counter module are pre-assembled as an integral member.

13. The atomization device of claim 1, wherein the lower housing comprises an observation window on a side wall of the lower housing, through which a position of the rotatable sleeve on the positioning shaft can be observed.

14. The atomization device of claim 1, wherein the lower housing is transparent.

15. The atomization device of claim 1, wherein the lower housing is rotatable relative to the upper housing to drive the container to move in the axial direction of the atomization device.

16. A counter module for an atomization device, wherein the atomization device has a container movable in an axial direction of the atomization device between a release position and an stretch position, wherein the stretch position is closer to a proximal end of the atomization device than the release position; and the counter module is configured to be mounted inside the atomization device for counting the movement of the container between the release position and the stretch position, wherein the counter module includes:

a positioning shaft extending from the inner bottom surface of the atomization device in a distal direction;

a rotatable sleeve which is sleeved on the positioning shaft and which is movable axially along the positioning shaft and rotatable about the positioning shaft, wherein the rotatable sleeve has a movable serrated surface facing the distal direction;

a touching member which is coupled to a distal end of the positioning shaft and which is movable axially along the positioning shaft but is not rotatable about the positioning shaft, and the touching member which includes a flange capable of operably engaging with the movable serrated surface; in response to that the container is moved towards the stretch position so that the flange is at least partially engaged with the movable serrated surface, the flange and the movable serrated surface, when mutually engaged, are configured to generate a circumferential force that makes the rotatable sleeve rotate;

a slidable ring, which is sleeved on the rotatable sleeve and which is threadedly coupled to rotatable sleeve, and the slidable ring is movable axially along the positioning shaft but is not rotatable about the positioning shaft; and a bias spring, which is mounted on the positioning shaft, one end of the bias spring configured to abut against the inner bottom surface of the atomization device, and the other end of the bias spring configured to abut against the rotatable sleeve; wherein the rotatable sleeve is configured to be pressed by the touching member and moves proximally to compress the bias spring in response to that the container moves from the release position to the stretch position; the rotatable sleeve is configured to be no longer pressed by the touching member so that the bias spring is released to push the rotatable sleeve to move axially in the distal direction in response to that the container moves from the stretch position to the release position; during at least a part of the axial movement of the rotatable sleeve, the circumferential force configured to be generated by the flange and the movable serrated surface, when are mutually engaged, is configured to drive the rotatable sleeve to rotate relative to the slidable ring and make the axial position of the slidable ring on the rotatable sleeve change.

* * * * *